United States Patent [19]

Nakagawa et al.

[11] 3,953,456

[45] Apr. 27, 1976

[54] CARBOSTYRIL DERIVATIVES AND PROCESS FOR PREPARING THE SAME

[75] Inventors: Kazuyuki Nakagawa, Tokushima; Shiro Yoshizaki, Komatsushima; Nanami Murakami; Hideo Mori, both of Tokushima, all of Japan

[73] Assignee: Otsuka Pharmaceutical Co., Ltd., Tokyo, Japan

[22] Filed: Dec. 14, 1973

[21] Appl. No.: 424,965

[30] Foreign Application Priority Data

Dec. 14, 1972 Japan............................ 47-125857

[52] U.S. Cl.................... 260/288 R; 260/289 R; 424/258
[51] Int. Cl.² ............................. C07D 215/22
[58] Field of Search .................. 260/288 R, 289 R

[56] References Cited
UNITED STATES PATENTS
3,340,266 9/1967 Howe et al..................... 260/288 R FOREIGN PATENTS OR APPLICATIONS
1,047,927 11/1966 United Kingdom............. 260/288 R
1,058,822 2/1967 United Kingdom............. 260/288 R
1,079,989 8/1967 United Kingdom............. 260/288 R

*Primary Examiner*—Richard J. Gallagher
*Assistant Examiner*—Mary Vaughn
*Attorney, Agent, or Firm*—Sughrue, Rothwell, Mion & Zinn

[57] ABSTRACT

2-Hydroxy-3-alkylaminopropoxycarbostyrils represented by the formula (I)

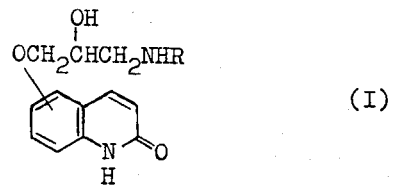

wherein R represents a straight or branched chain alkyl group having 1 to 4 carbon atoms useful as β-adrenergic blocking agents and a process for preparing the same are disclosed.

6 Claims, No Drawings

CARBOSTYRIL DERIVATIVES AND PROCESS FOR PREPARING THE SAME

BACKGROUND OF THE INVENTION

1. FIELD OF THE INVENTION

This invention relates to 5-, 6-, 7- or 8-(2-hydroxy-3-alkylamino)propoxycarbostyrils useful as β-adrenergic blocking agents and a process for preparing the same.

2. DESCRIPTION OF THE PRIOR ART

It is well known that certain carbostyril derivatives exhibit useful pharmaceutical activities. Representative compounds of this type have been disclosed in *Journal of Medical Chemistry*, Vol. 15, No. 3, pp 260–266 (1972), Japanese Patent Publication No. 38789/1971, and *Chemical Abstracts*, 62, 1b 212e (1965), etc. However, these prior art references do not teach that the compounds having a (2-hydroxy-3-alkylamino)-propoxy group at 5-, 6-, 7- or 8-position of a carbostyril moiety possess an excellent β-adrenergic blocking activity.

The present inventors have found that novel 3,4-dihydrocarbostyril derivatives having a 3-substituted-aminopropoxy group at 5-, 6-, 7- or 8-position of the carbostyril moiety possess a useful β-adrenergic blocking activity as described in our copending application Ser. No. 325,981 filed on Jan. 23, 1973.

As a result of further investigation on other derivatives, it was unexpectedly found that compounds having a (2-hydroxy-3-alkylamino)propoxy group at 5-, 6-, 7- or 8-position of the carbostyril moiety exhibit the above pharmacological activity and that these compounds can easily be prepared from the corresponding 5-, 6-, 7- or 8-(2,3-epoxy)propoxycarbostyril or 5-, 6-, 7- or 8-(2-hydroxy-3-halo)propoxycarbostyril or a mixture thereof, retaining the β-adrenergic blocking pharmacological activity.

SUMMARY OF THE INVENTION

The present invention provides 5-, 6-, 7- or 8-(2-hydroxy-3-alkylamino)propoxycarbostyrils having the formula (I)

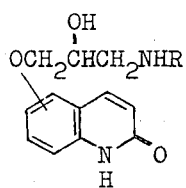

(I)

wherein R represents a straight or branched chain alkyl group having 1 to 4 carbon atoms.

This invention also provides a process for preparing the above 5-, 6-, 7- or 8-(2-hydroxy-3-alkylamino)-propoxycarbostyrils represented by the formula (I) which comprises reacting a 5-, 6-, 7- or 8-substituted carbostyril represented by the formula (II)

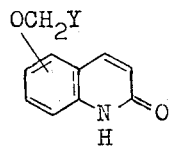

(II)

wherein Y represents a

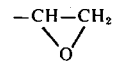

group or a

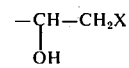

group in which X represents a halogen atom, with a lower alkylamine having 1 to 4 carbon atoms. The compounds of the formula (I) are useful as β-adrenergic blocking agents.

DETAILED DESCRIPTION OF THE INVENTION

The 5-, 6-, 7- or 8-(2-hydroxy-3-alkylamino)propoxycarbostyrils represented by the formula (I) above and the acid addition salts thereof exhibit a β-adrenergic blocking activity and are useful as pharmaceuticals for treating disorders in coronary sclerosis such as arrhythmia, tachycardia, angina pectoris, coronary insufficiency, hypertension, etc.

The acid addition salts of the carbostyril derivatives of the present invention can be easily prepared using well known procedures by reaction with inorganic and organic acids. Typical examples of pharmaceutically acceptable acid addition salts are the hydrochlorides, hydrobromides, sulfates, phosphates, oxalates, maleates, citrates and the like.

The compound represented by the formula (II) above which is used as a starting material in the process of the present invention is also a novel compound and can be prepared by reacting a known hydroxycarbostyril and an epihalohydrin in the presence of a basic catalyst.

The 5-, 6-, 7- and 8-hydroxycarbostyrils used for the preparation of the starting material used in the present invention are described in *Berichte*, Vol. 20, page 2172, 1887; *Journal of Organic Chemistry*, Vol. 36, pp 3490–3493, 1971 and ibid, Vol. 33, pp 1089–1092, 1968. Briefly, 5-hydroxycarbostyril can be prepared by fusing 5-hydroxyquinoline with a caustic alkali such as sodium hydroxide or potassium hydroxide, and 8-hydroxycarbostyril can be prepared by reacting 8-hydroxyquinoline with hydrogen peroxide in glacial acetic acid to produce 8-hydroxyquinoline 1-oxide which is then refluxed in acetic anhydride to obtain acetoxycarbostyril and hydrolyzing the resulting acetoxycarbostyril with concentrated hydrochloric acid to give the desired 8-hydroxycarbostyril. The 6- and 7-hydroxycarbostyrils can be prepared in a similar manner to those described above.

Suitable examples of the epihalohydrin are epibromohydrin, epichlorohydrin or epiiodohydrin, preferably epichlorohydrin. Suitable basic compounds are alkali metals, alkali metal hydroxides, alkali metal carbonates and organic bases. Preferred examples of the basic compounds are sodium metal, potassium metal, sodium hydroxide, potassium hydroxide, sodium carbonate, potassium carbonate, piperidine, piperazine, pyridine, lower alkylamines such as diethylamine, triethylamine, methylamine and the like. The reaction between the hydroxycarbostyril and the epihalohydrin can be carried out in the absence of solvents, but preferably is carried out in the presence of an inert solvent, for example, lower alkanols, water, lower alkyl acetate and ketones. Suitable examples of lower alkanols are methanol, ethanol, isopropanol, n-propanol, n-butanol and the like. Suitable examples of lower alkyl acetates are ethyl acetate, methyl acetate, propyl acetate, and the like. Suitable examples of ketones are acetone and methyl ethyl ketone. Although any combination of the solvent and basic compound can be used, it is preferred to select the solvent depending upon the basic compound used. In preferred embodiments, lower alkanols are used with alkali metals and water with alkali metal hydroxides. When the basic compounds are organic bases, the reaction can be carried out without using any solvent or with a lower alkanol, lower alkyl acetate or ketone.

The reaction temperature can range from 0° to the boiling point of the solvent used, preferably from 50° to a boiling point of the solvent, for a period of from 4 to 6 hours, preferably from 4 to 5 hours, when alkali metals or alkali metal hydroxides are used as the basic compound, and the reaction temperature can range from 0° to 120°C, preferably 80° to 120°C for a period of from 4 to 6 hours, preferably 5 to 6 hours, when organic bases are used as the basic compound. The reaction is usually carried out at atmospheric pressure. In this reaction, both 5-, 6-, 7- or 8-(2,3-epoxy)propoxycarbostyril derivatives and 5-, 6-, 7- or 8(2-hydroxy3-halo)propoxycarbostyril derivatives (formula (II) wherein Y is

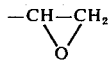

and

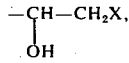

respectively) are obtained as a reaction product. The proportion of the 2,3-epoxy compound and 2-hydroxy-3-halo compound in the product varies with the type of the basic compounds used or with the position to which such a propoxy substituent is attached. The former compound is produced predominantly when the reaction is conducted in the presence of strongly basic compounds such as alkali metals and alkali metal hydroxides as recited above or in the case of producing a 5-substituted carbostyril compound, and the latter compound is produced predominantly when the reaction is conducted in the presence of weakly basic compounds such as organic bases, in particular piperidine, and the epihalohydrin is used in excess or in the case of producing 8-substituted carbostyril compound.

These products can be separated from each other by conventional procedures, for example, fractional crystallization, but preferably are separated by column chromatography using a column packed with active alumina, silica gel or the like. The product thus obtained, i.e., a mixture of 2,3-epoxy and 3-halo compounds, can be used as a starting material for the preparation of the novel compounds of the present invention. Alternatively, the components can be separated and each used as a starting material. In either case, the reaction can be effected in the same manner without adversely affecting the purity and yield of the desired product.

The reaction between a 5-substituted carbostyril and a lower alkylamine can be carried out using 2 to 40 moles, preferably from 2 to 5 moles per one mole of a 5-substituted carbostyril. Suitable examples of the lower alkylamine are mono- or disubstituted alkylamines having 1 to 4 carbon atoms such as methylamine, dimethylamine, ethylamine, isopropylamine, t-butylamine, sec-butylamine and the like. This reaction can be carried out in the presence or absence of a solvent, but it is preferred to use an organic solvent such as an alcohol, e.g., methanol, ethanol, isopropanol, an ester, e.g., ethyl acetate, an ether, e.g., ethyl ether, chloroform and the like. when the reaction is carried out in the absence of an organic solvent, an excess of the lower alkylamine reactant also serves as a reaction medium. In either case, the reaction proceeds at a temperature of from 0° to the refluxing temperature of the reaction system, for example, up to about 85°C, but it is preferable to heat the reaction system at an elevated temperature, for example 45° to 65°C in order to accelerate the reaction. The reaction is generally completed within a period of 2 to 8 hrs, more generally, 3 to 5 hrs. After completion of the reaction, the compound (II) thus obtained can be isolated and purified using known techniques such as distillation, recrystallization, extraction and the like. The recrystallization and extraction can suitably be effected using acetone, methanol, ethyl acetate, chloroform and the like.

Representative compounds of this invention include the following free bases and their pharmaceutically acceptable acid addition salts:

5-(2-hydroxy-3-isopropylamino)propoxycarbostyril,
5-(2-hydroxy-3-tert-butylamino)propoxycarbostyril,
8-(2-hydroxy-3-tert-butylamino)propoxycarbostyril,
8-(2-hydroxy-3-isopropylamino)propoxycarbostyril, and
8-(2-hydroxy-3-sec-butylamino)propoxycarbostyril.

The present invention will be further illustrated by reference to the following Examples, but they are not to be construed as limiting the present invention. Unless otherwise indicated, all parts, percents, ratios, and the like are by weight.

EXAMPLE 1

1.0 ml of isopropylamine and 10 ml of methanol were added to 1.0 g of 5-(2,3-epoxy)propoxycarbostyril having a melting point of 181° – 184°C and the resulting mixture was heated at 50°C for a period of 4 hours followed by concentration to dryness. A large excess of dilute hydrochloric acid (1 to 10% by volume) was added to the residue and any insoluble substances were removed by filtration. The aqueous layer separated was concentrated and the residue was recrystallized from ethanol to obtain 1.1 g of 5-(2-hydroxy-3-isopropylamino)propoxycarbostyril hydrochloride as colorless amorphous crystals having a melting point of 251° – 253°C.

EXAMPLE 2

1.0 ml of tert-butylamine and 10 ml of ethanol were added to 1.0 g of 5-(2,3-epoxy)propoxycarbostyril and the resulting mixture was allowed to stand for 24 hours followed by concentration to dryness. Dilute hydrochloric acid was added to the residue and any insoluble substances were removed by filtration. The aqueous layer separated was concentrated and the residue was recrystallized from ethanol to obtain 1.0 g of 5-(2-hydroxy-3-tert-butylamino)propoxycarbostyril hydrochloride as colorless amorphous crystals having a melting point of 295° – 298°C.

EXAMPLE 3

1.0 ml of tert-butylamine and 10 ml of methanol were added to 1.0 g of 5-(2-hydroxy-3-chloro)propoxycarbostyril, and the resulting mixture was heated at the reflux temperature for 4 hours followed by concentration to dryness. Dilute hydrochloric acid was added to the residue and any insoluble substances were removed by filtration. The aqueous layer separated was concentrated and the residue was recrystallized from ethanol to obtain 1.0 g of 5-(2-hydroxy-3-tert-butylamino)-propoxycarbostyril hydrochloride as colorless amorphous crystals having a melting point of 295° – 298°C.

EXAMPLE 4

2.0 g of 8-(2-hydroxy-3-chloro)propoxycarbostyril as prepared in Reference Example 2 and 6.7 g of tert-butylamine were added to 50 ml of methanol, and the resulting mixture was heated at a refluxing temperature for 4.5 hours while stirring. After completion of the reaction, the reaction mixture was filtered and the filtrate was concentrated to give 283 mg (31% yield) of 8-(2-hydroxy-3-tert-butylamino)propoxycarbostyril having a melting point of 200.5° – 201.5°C after recrystallization from acetone.

Analysis Calcd. for $C_{16}H_{22}O_3N$: C, 66.18; H, 7.64; N, 9.65(%). Found: C, 66.41; H, 7.88; N, 9.64(%).

EXAMPLE 5

2.0 g of 8-(2-hydroxy-3-chloro)propoxycarbostyril as prepared in Reference Example 2 and 5.4 g of isopropylamine were added to 40 ml of methanol, and the resulting mixture was heated at the refluxing temperature for 16 hours. After completion of the reaction, the reaction mixture was filtered and the filtrate was concentrated to give 720 mg (42% yield) of 8-(2-hydroxy-3-isopropylamino)propoxycarbostyril having a melting point of 177.5° – 178°C after recrystallization from acetone.

Anaylsis: Calcd. for $C_{15}H_{20}O_3N_2$: C, 65.19; H, 7.30; N. 10.14(%). Found: C, 65.59; H, 7.84; N, 10.11(%).

EXAMPLE 6

2.0 g of 8-(2-hydroxy-3-chloro)propoxycarbostyril as prepared in Reference Example 2 and 5.4 g of isopropylamine were added to 40 ml of methanol, and the resulting mixture was heated at a refluxing temperature for 13 hours while stirring. After completion of the reaction, the reaction mixture was filtered and the filtrate was concentrated to give 741 mg (36% yield) of 8-(2-hydroxy-3-sec-butylamino)propoxycarbostyril having a melting point of 140.5° – 142°C after recrystallization from acetone.

Analysis Calcd. for $C_{16}H_{22}O_3N_2$: c, 66.18; H, 7.64; N, 9.65(%). Found: C, 66.34; H, 7.98; N, 9.86(%).

REFERENCE EXAMPLE 1

0.6 g of sodium hydroxide was dissolved in 40 ml of water, and 2.0 g of 5-hydroxycarbostyril and 2.5 g of epichlorohydrin were added to the solution. The mixture was stirred at a temperature of from 60° to 70°C for 5 hours followed by cooling to precipitate the product. The precipitated crystals were washed with water, dissolved in ethanol and then subjected to thin layer chromatography using acetone as an eluate to obtain two spots having a Rf value of 0.58 and 0.65, respectively. The spot having a Rf value of 0.58 was extracted with ethanol and crystallized to obtain 5-(2,3-epoxy)-propoxycarbostyril which was used as the starting material in Examples 1 and 2. The spot having a Rf value of 0.65 was worked up in the same manner as described above to obtain 5-(2-hydroxy-3-chloro)propoxycarbostyril which was used as the starting material in Example 3.

REFERENCE EXAMPLE 2

2.0 g of 8-hydroxycarbostyril was added to 200 ml of an ethanolic solution of 8.5 g of sodium ethoxide, and the resulting mixture was stirred for one hour at a temperature of 50°C. 40 g of epichlorohydrin was then added to the mixture followed by allowing to react for 10 hours at a temperature of 50°C. After completion of the reaction, the reaction mixture was filtered to isolate crystalline 8-(2-hydroxy-3-chloro)propoxycarbostyril which was then washed with water and dried. Yield, 6.5 g (20.5%). Melting point, 228° – 231°C (recrystallized from chloroform).

Analysis: Calcd. for $C_{12}H_{12}O_3NCl$: C, 56.82; H, 4.77; N, 5.52(%). Found: C, 56.72; H, 5.00; N, 5.62(%).

REFERENCE EXAMPLE 3

The antagonistic activity of the compounds of this invention against isoprenaline was determined using the β-blockers screening method (C. E. Powell, I. H. Slater : J. Pharmac., 122, 480 (1958)).

Male mongrel adult dogs, weighing 13 to 20 Kg were anesthesized with 30 mg/Kg of body weight of pentabarbital sodium administered intravenously. Each of the test compounds was then administered to the anesthesized dog at a dosage level of 30γ or 100γ/Kg of body weight from the femoral vein and after 5 minutes isoprenaline was administered to the dog through the femoral vein at a dosage level of 0.3 γ/Kg of body weight. the blood pressure and the pulse (H.R.) were then recorded on a polygraph through a pressure transducer and a tachometer operated by the R wave of the electrocardiograph, respectively, to determine % inhibitory activity of the test compound against the pulse increase and the pressure reduction induced by isoprenaline. The results obtained are shown in Table below.

Table

| Test Compound | Dosage Level (γ/Kg) | Antagonistic Activity Against Isoprenaline (% Inhibition)* | |
|---|---|---|---|
| | | Blood Pressure | Pulse |
| 5-(2-hydroxy-3-isopropylamino)- | 30 | 89.2% | 87.6% |
| 5-(2-hydroxy-3-tert-butylamino)- | 30 | 97.9% | 96.1% |
| 8-(2-hydroxy-3-isopropylamino)- | 100 | 66.2% | 57.4% |
| 8-(2-hydroxy-3-tert-butylamino)- | 100 | 78.3% | 72.6% |
| 8-(2-hydroxy-3-sec-butylamino)- | 100 | 51.8% | 42.1% |

*The pulse increase and the pressure reduction induced by the administration of isoprenaline alone are referred to as 100%.

Also, the acute toxicity in rat (Wister strain) was determined in a standard manner with respect to representative compounds of this invention. The LD$_{50}$ (50% lethal dose) are as follows:

| Compound | LD$_{50}$ (mg/Kg) | |
|---|---|---|
| | i.v. | p.o. |
| 5-(2-hydroxy-3-isopropylamino)propoxy-carbostyril | 162 | 2000 |
| 5-(2-hydroxy-3-tert-butylamino)propoxy-carbostyril | 136 | 1800 |
| 8-(2-hydroxy-3-isopropylamino)propoxy-carbostyril | 178 | 2000 |
| 8-(2-hydroxy-3-tert-butylamino)propoxy-carbostyril | 148 | 1800 |
| 8-(2-hydroxy-3-sec-butylamino)propoxy-carbostyril | 143 | 1900 |

While the present invention has been described in detail with reference to specific embodiments thereof, it is apparent to one skilled in the art that various changes and modifications can be made therein without departing from the spirit and the scope of the present invention.

What is claimed is:

1. A 5- or 8- (2-Hydroxy-3-alkylamino)propoxycarbostyril compound represented by the formula (I):

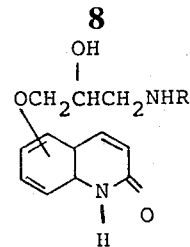

(I)

wherein R represents a straight or branched alkyl group having 1 to 4 carbon atoms, and the pharmaceutically acceptable acid addition salts thereof.

2. 5-(2-Hydroxy-3-isopropylamino)propoxycarbostyril according to claim 1.
3. 5-(2-Hydroxy-3-tert-butylamino)propoxycarbostyril according to claim 1.
4. 8-(2-Hydroxy-3-tert-butylamino)propoxycarbostyril according to claim 1.
5. 8-(2-Hydroxy-3-isopropylamino)propoxycarbostyril according to claim 1.
6. 8-(2-Hydroxy-3-sec-butylamino)propoxycarbostyril according to claim 1.

* * * * *